United States Patent [19]

Davis

[11] Patent Number: 5,661,145

[45] Date of Patent: Aug. 26, 1997

[54] COMBINATION OF A CHOLESTEROL BIOSYNTHESIS INHIBITOR AND A β-LACTAM CHOLESTEROL ABSORPTION INHIBITOR

[75] Inventor: Harry R. Davis, Berkeley Heights, N.J.

[73] Assignee: Schering Corporation, Kenilworth, N.J.

[21] Appl. No.: 454,348

[22] PCT Filed: Dec. 21, 1993

[86] PCT No.: PCT/US93/12291

§ 371 Date: Jun. 20, 1995

§ 102(e) Date: Jun. 20, 1995

[87] PCT Pub. No.: WO94/14433

PCT Pub. Date: Jul. 7, 1994

Related U.S. Application Data

[63] Continuation-in-part of Ser. No. 995,488, Dec. 23, 1992, abandoned.

[51] Int. Cl.$^6$ .................. A61K 31/395; A61K 31/35; A61K 31/21

[52] U.S. Cl. .................. 514/210; 514/451; 514/460; 514/510; 514/824

[58] Field of Search .................. 514/210, 451, 514/460, 510, 824

[56] References Cited

U.S. PATENT DOCUMENTS 4,680,391 7/1987 Firestone et al. .................. 540/355
4,983,597 1/1991 Yang et al. .................. 514/210
5,120,729 6/1992 Chabala et al. .................. 514/210

FOREIGN PATENT DOCUMENTS

92/05972 2/1993 WIPO .

OTHER PUBLICATIONS

CA 114:101559, Ram et al., 1990.
Witzum, *Circulation*, 80, 5 (1989), pp. 1101–1114.
Illingworth, *Drugs*, 36(Supp. 3) (1988), pp. 63–71.
Allain, et al, *Clin. Chem.*, 20, (1974), pp. 470–475.
Schnitzer-Polokoff, et al, *Comp. Biochem. Physiol.*, 99A (1991), pp. 665–670.
Horie, et al, *Atherosclerosis*, 88 (1991), pp. 183–192.
Baxter, et al, J. *Biological Chem.*, 267, 17(1992), pp. 11705–11708.
*Current Drugs: Anti–Atherosclerotic Agents*—Summary Factfile, May, 1992.
*Lancet*, 344 (1994), pp. 1383–1389.

Primary Examiner—Kimberly Jordan
Attorney, Agent, or Firm—Anita W. Magatti

[57] ABSTRACT

Methods of reducing plasma cholesterol levels and treating or preventing atherosclerosis comprising administering an effective amount of a combination of a cholesterol biosynthesis inhibitor and a β-lactam cholesterol absorption inhibitor, as well as pharmaceutical compositions and kits useful in those methods, are disclosed.

7 Claims, No Drawings

COMBINATION OF A CHOLESTEROL BIOSYNTHESIS INHIBITOR AND A β-LACTAM CHOLESTEROL ABSORPTION INHIBITOR

The present application is the United States national application corresponding to International application Ser. No. PCT/US 93/12291, filed Dec. 21, 1993 and designating the United States, which PCT application is in turn a continuation-in-part of U.S. application Ser. No. 07/995,488, filed Dec. 23, 1992, now abandoned, the benefit of which applications are claimed pursuant to the provisions of 35 U.S.C. 120,363 and 365 (C).

BACKGROUND

The present invention relates to a combination of a cholesterol biosynthesis inhibitor and a β-lactam cholesterol absorption inhibitor useful in reducing plasma cholesterol levels, and to a method of treating or preventing atherosclerosis comprising administering the claimed combination.

Plasma cholesterol levels have been positively correlated with the incidence of clinical events associated with coronary heart disease. The regulation of whole-body cholesterol homeostasis in humans and animals involves modulation of cholesterol biosynthesis, bile acid biosynthesis, and the catabolism of the cholesterol-containing plasma lipoproteins. The liver is the major organ responsible for cholesterol biosynthesis and catabolism and, for this reason, it is a prime determinant of plasma cholesterol levels. The liver is the site of synthesis and secretion of very low density lipoproteins (VLDL) which are subsequently metabolized to low density lipoproteins (LDL) in the circulation. LDL are the predominant cholesterol-carrying lipoproteins in the plasma and an increase in their concentration is correlated with increased atherosclerosis.

Another major factor in determining cholesterol homeostasis is the absorption of cholesterol in the small intestine. On a daily basis, the average human consuming a Western diet eats 300 to 500 mg of cholesterol. In addition, 600 to 1000 mg of cholesterol can traverse the intestines each day. This latter cholesterol is a component of bile and is secreted from the liver. The process of cholesterol absorption is complex and multifaceted. It has been reported that approximately 50% of the total cholesterol within the intestinal lumen is absorbed by the cells lining the intestines (i.e., enterocytes). This cholesterol includes both diet-derived and bile- or hepatic-derived cholesterol. Much of the newly-absorbed cholesterol in the enterocytes is esterified by the enzyme acyl-CoA:cholesterol acyltransferase (ACAT). Subsequently, these cholesteryl esters are packaged along with triglycerides and other components (i.e., phospholipids, apoproteins) into another lipoprotein class, chylomicrons.

Chylomicrons are secreted by intestinal cells into the lymph where they can then be transported to the blood. Virtually all of the cholesterol absorbed in the intestines is delivered to the liver by this route. When cholesterol absorption in the intestines is reduced, by whatever means, less cholesterol is delivered to the liver. The consequence of this action is a decreased hepatic lipoprotein (VLDL) production and an increase in the hepatic clearance of plasma cholesterol, mostly as LDL. Thus, the net effect of an inhibition of intestinal cholesterol absorption is a decrease in plasma cholesterol levels.

Beta-lactams such as (3R-4S)-1,4-bis-(4-methoxyphenyl)-3-(3-phenylpropyl)-2-azetidinone disclosed in PCT/US92/05972 are potent inhibitors of intestinal cholesterol absorption, leading to decreased plasma cholesterol levels in several animal species (hamsters, rats, rabbits, monkeys).

The inhibition of cholesterol biosynthesis by 3-hydroxy-3-methylglutaryl coenzyme A reductase (EC1.1.1.34) inhibitors has been shown to be an effective way to reduce plasma cholesterol (Witzum, 1989) and reduce atherosclerosis. Combination therapy of an HMG CoA reductase inhibitor and a bile acid sequestrant has been demonstrated to be more effective in human hyperlipidemic patients than either agent in monotherapy (Illingworth, 1988).

We have unexpectedly found that a combination of a beta-lactam cholesterol absorption inhibitor and the HMG CoA reductase inhibitor lovastatin (MEVACOR™) results in a greater decrease in plasma cholesterol than either agent alone in chow-fed dogs and rhesus monkeys, and in cholesterol-fed hamster and rabbits. These findings were unexpected because HMG CoA reductase inhibitors alone do not lower plasma cholesterol levels in hamster and monkeys.

SUMMARY OF THE INVENTION

The present invention relates to a method of reducing plasma cholesterol levels comprising administering to a mammal in need of such treatment an effective amount of a combination of a cholesterol biosynthesis inhibitor and a β-lactam cholesterol absorption inhibitor. The invention also relates to a method of treating or preventing atherosclerosis comprising administering an effective amount of a combination of a cholesterol biosynthesis inhibitor and a β-lactam cholesterol absorption inhibitor to a mammal in need of such treatment. That is, the present invention relates to the use of a β-lactam cholesterol absorption inhibitor for combined use with a cholesterol biosynthesis inhibitor (and, similarly, use of a cholesterol biosynthesis inhibitor for combined use with a β-lactam cholesterol absorption inhibitor) to treat or prevent athersclerosis or to reduce plasma cholesterol levels In a third aspect, the invention relates to a pharmaceutical composition comprising an effective amount of a cholesterol biosynthesis inhibitor, a β-lactam cholesterol absorption inhibitor and a pharmaceutically acceptable carrier. In still another aspect, the invention relates to a kit comprising in one container an effective amount of a cholesterol biosynthesis inhibitor in a pharmaceutically acceptable carrier, and in a separate container, an effective amount of a β-lactam cholesterol absorption inhibitor in a pharmaceutically acceptable carrier.

DETAILED DESCRIPTION

Cholesterol biosynthesis inhibitors for use in the combination of the present invention include HMG CoA reductase inhibitors such as lovastatin, pravastatin, fluvastatin, simvastatin and CI-981; HMG CoA synthetase inhibitors, for example L-659,699 ((E,E-11-[3'R-(hydroxymethyl)-4'-oxo-2'R-oxetanyl]-3,5,7R-trimethyl-2,4-undecadienoic acid); squalene synthesis inhibitors, for example squalestatin 1; and squalene epoxidase inhibitors, for example, NB-598 ((E)-N-ethyl-N-(6,6-dimethyl-2-hepten-4-ynyl)-3-[(3,3'-bithiophen-5-yl)methoxy]benzene-methanamine hydrochloride). Preferred HMG CoA reductase inhibitors are lovastatin, pravastatin and simvastatin.

β-lactam cholesterol absorption inhibitors include those identified as novel compounds in formula I of PCT/US92/05972, filed Jul. 21, 1992, and published as WO93/02048 on Feb. 4, 1993 as well as those identified in formula II of that PCT application for use in lowering cholesterol. Said PCT application is incorporated herein by reference; formulas I and II are shown herein as follows:

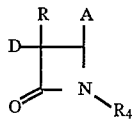

wherein

A is
—CH═CH—B;
—C≡C—B;
—(CH$_2$)$_p$—X—B, wherein p is 0, 1 or 2 and X is a bond, —NH— or —S(O)$_{0-2}$—;
heteroaryl, benzofused heteroaryl, W-substituted heteroaryl or W-substituted benzofused heteroaryl, wherein heteroaryl is selected from the group consisting of pyrrolyl, pyridinyl, pyrimidinyl, pyrazinyl, triazinyl, imidazolyl, thiazolyl, pyrazolyl, thienyl, oxazolyl and furanyl, and for nitrogen-containing heteroaryls, the N-oxides thereof, and wherein W is 1–3 substituents on the ring carbon atoms selected from the group consisting of lower alkyl, hydroxy lower alkyl, lower alkoxy, alkoxyalkyl, alkoxyalkoxy, alkoxycarbonylalkoxy, (lower alkoxy-imino)lower alkyl, lower alkanedioyl, lower alkyl lower alkanedioyl, allyloxy,—CF$_3$, —OCF$_3$, benzyl, R$_{14}$-benzyl, benzyloxy, R$_{14}$-benzyloxy, phenoxy, R$_{14}$-phenoxy, dioxolanyl, NO$_2$, —NR$_{10}$R$_{11}$, NR$_{10}$R$_{11}$(lower alkyl)-, NR$_{10}$R$_{11}$(lower alkoxy)-, OH, halogeno, —NHC(O)OR$_5$, —NHC(O)R$_5$, R$_6$O$_2$SNH—, (R$_6$O$_2$S)$_2$N—, —S(O)$_2$NH$_2$, —S(O)$_{0-2}$R$_{10}$, tert-butyldimethylsilyloxymethyl, —C(O)R$_{12}$ and

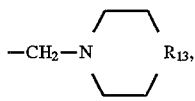

and wherein the substituents on the substituted heteroaryl ring nitrogen atoms, when present, are selected from the group consisting of lower alkyl, lower alkoxy, —C(O)OR$_5$, —C(O)R$_5$, OH, NR$_{10}$R$_{11}$(lower alkyl)-, NR$_{10}$R$_{11}$(lower alkoxy)-, —S(O)$_2$NH$_2$ and 2-(trimethylsilyl)ethoxymethyl;

—C(O)—B; or

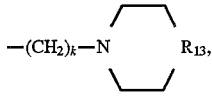

wherein k is 1 or 2;

D is B'—(CH$_2$)$_m$C(O)—, wherein m is 1, 2, 3, 4 or 5;
B'—(CH$_2$)$_q$—, wherein q is 2, 3, 4, 5 or 6;
B'—(CH$_2$)$_e$—Z—(CH$_2$)$_r$—, wherein Z is —O—, —C(O)—, phenylene, —NR$_8$— or —S(O)$_{0-2}$—, e is 0, 1, 2, 3, 4 or 5 and r is 1, 2, 3, 4 or 5, provided that the sum of e and r is 1, 2, 3, 4, 5 or 6;
B'—(C$_2$-C$_6$ alkenylene)-; B'—(C$_4$-C$_6$ alkadienylene)-;
B'—(CH$_2$)$_t$—Z—(C$_2$-C$_6$ alkenylene)-, wherein Z is as defined above, and wherein t is 0, 1, 2 or 3, provided that the sum of t and the number of carbon atoms in the alkenylene chain is 2, 3, 4, 5 or 6;
B'—(CH$_2$)$_f$—V—(CH$_2$)$_g$—, wherein V is C$_3$-C$_6$ cycloalkylene, f is 1, 2, 3, 4 or 5 and g is 0, 1, 2, 3, 4 or 5, provided that the sum of f and g is 1, 2, 3, 4, 5 or 6;

B'—(CH$_2$)$_t$—V—(C$_2$-C$_6$ alkenylene)- or B'—(C$_2$-C$_6$ alkenylene)—V—(CH$_2$)$_t$—, wherein V and t are as defined above, provided that the sum of t and the number of carbon atoms in the alkenylene chain is 2, 3, 4, 5 or 6;

B'—(CH$_2$)$_a$—Z—(CH$_2$)$_b$—V—(CH$_2$)$_d$—, wherein Z and V are as defined above and a, b and d are independently 0, 1, 2, 3, 4, 5 or 6, provided that the sum of a, b and d is 0, 1, 2, 3, 4, 5 or 6;

T—(CH$_2$)$_s$—, wherein T is cycloalkyl of 3–6 carbon atoms and s is 1, 2, 3, 4, 5 or 6; or naphthylmethyl, heteroarylmethyl, or W-substituted heteroarylmethyl, wherein heteroaryl and W are as defined above;

B is

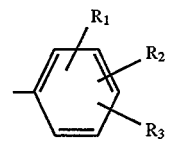

B' is naphthyl, heteroaryl or W-substituted heteroaryl, wherein heteroaryl is as defined above, or

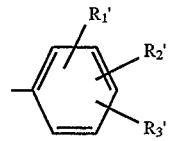

R is hydrogen, fluoro, C$_1$-C$_{15}$ alkyl, C$_1$-C$_{15}$ alkenyl, C$_1$-C$_{15}$ alkynyl, or B—(CH$_2$)$_h$—, wherein h is 0, 1, 2, or 3;

R$_1$, R$_2$ and R$_3$ are independently selected from the group consisting of H and W, provided that when W is halogeno, it is o-halogeno or m-haolgeno; or R$_1$ is hydrogen and R$_2$ and R$_3$, together with adjacent carbon atoms to which they are attached, form a dioxolanyl ring;

R$_1$', R$_2$' and R$_3$' are independently selected from the group consisting of H and W; or R$_1$' is hydrogen and R$_2$' and R$_3$', together with adjacent carbon atoms to which they are attached, form a dioxolanyl ring;

R$_4$ is

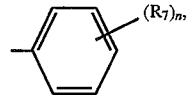

wherein n is 0, 1, 2 or 3, indanyl, benzofuranyl, benzodioxolyl, tetrahydronaphthyl, pyridyl, pyrazinyl, pyrimidinyl or quinolyl;

R$_5$ is lower alkyl, phenyl, R$_{14}$-phenyl, benzyl or R$_{14}$-benzyl;

R$_6$ is OH, lower alkyl, phenyl, benzyl, R$_{14}$-phenyl or R$_{14}$-benzyl;

R$_7$ is lower alkyl, lower alkoxy, OH, halogeno, —NR$_{10}$R$_{11}$, —NHC(O)OR$_5$, —NHC(O)R$_5$, NO$_2$, —CN, —N$_3$, —SH, —S(O)$_{0-2}$-(lower alkyl), —COOR$_9$, —CONR$_{10}$R$_{11}$, —COR$_{12}$, phenoxy, benzyloxy, —OCF$_3$, or tert-butyldimethylsilyloxy, and where n is 2 or 3, the R$_7$ groups can be the same or different;

$R_8$ is H, lower alkyl, phenyl lower alkyl, or —C(O)$R_9$;

$R_9$ is H, lower alkyl, phenyl or phenyl lower alkyl;

$R_{10}$ and $R_{11}$ are independently selected from H and lower alkyl;

$R_{12}$ is H, OH, alkoxy, phenoxy, benzyloxy,

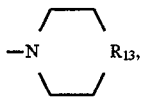

—N$R_{10}R_{11}$, lower alkyl, phenyl or $R_{14}$-phenyl;

$R_{13}$ is —O—, —CH$_2$—, —NH— or —N(lower alkyl)-; and $R_{14}$ is 1–3 groups independently selected from the group consisting of lower alkyl, lower alkoxy, —COOH, NO$_2$, —N$R_{10}R_{11}$, OH or halogeno;

or a pharmaceutically acceptable salt thereof.

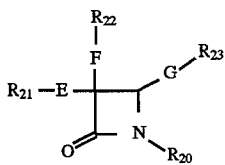

II wherein $R_{20}$ is phenyl, W-substituted phenyl, naphthyl, W-substituted naphthyl, benzodioxolyl, heteroaryl, W-substituted heteroaryl, benzofused heteroaryl and W-substituted benzofused heteroaryl, wherein heteroaryl is as defined above;

$R_{21}$, $R_{22}$ and $R_{23}$ are independently selected from H or $R_{20}$;

W is 1 to 3 substituents independently selected as defined above;

E, F and G are independently a bond; $C_3$–$C_6$ cycloalkylene; $C_1$–$C_{10}$ alkylene; $C_1$–$C_{10}$ alkenylene; $C_1$–$C_{10}$ alkynylene; an alkylene, alkenylene or alkynylene chain as defined substituted by one or more substituents independently selected from the group consisting of phenyl, W-substituted phenyl, heteroaryl and W-substituted heteroaryl, wherein heteroaryl is as defined above; an alkylene, alkenylene or alkynylene chain as defined interrupted by one or more groups independently selected from the group consisting of —O—, —S—, —SO—, —SO$_2$—, —N$R_8$—, —C(O)—, $C_3$–$C_6$ cycloalkylene, phenylene, W-substituted phenylene, heteroarylene and W-substituted heteroarylene; or an interrupted alkylene, alkenylene or alkynylene chain as defined substituted by one or more substituents independently selected from the group consisting of phenyl, W-substituted phenyl, heteroaryl and W-substituted heteroaryl; or one of $R_{21}$—E and $R_{22}$—F is selected from the group consisting of halogeno, OH, lower alkoxy, —OC(O)$R_5$, —N$R_{10}R_{11}$, —SH or —S(lower alkyl);

and wherein $R_5$, $R_6$, and $R_8$–$R_{14}$ are as defined above; provided that when G is a bond, $R_{23}$ is not H, and provided that when $R_{23}$ is W-substituted phenyl, W is not p-halogeno;

or a pharmaceutically acceptable salt thereof.

Preferred are compounds of formula I wherein R is H. Another group of preferred compounds of formula I is that wherein D is: B'—(CH$_2$)$_q$—, B'—(CH$_2$)$_e$—Z—(CH$_2$)$_r$—, B'—(C$_2$–C$_6$ alkenylene)-, or B'—(CH$_2$)$_f$—V—(CH$_2$)$_g$—, wherein B', Z, V, q, e, r, f, and g are as defined above. A third group of preferred compounds of formula I is that wherein $R_4$ is phenyl, $R_7$-substituted phenyl or indanyl. Still another group of preferred compounds of formula I is that wherein A is —(CH$_2$)$_p$—X—B, wherein X, B and p are as defined above.

Especially preferred are compounds of formula I wherein D is: B'—(CH$_2$)$_q$—, wherein B' is phenyl and q is 3 or 4; B'—(CH$_2$)$_e$—Z—(CH$_2$)$_r$—, wherein B' is p-fluorophenyl or p-methoxyphenyl, e is zero, Z is —O—, and r is 2; B'—C$_2$–C$_6$ alkenylene)- is 3-phenyl-1-propenyl; or B'—(CH$_2$)$_f$—V—(CH$_2$)$_g$—, wherein B' is phenyl, f is 1, V is cyclopropylene, and g is zero. Also especially preferred are compounds of formula I wherein A is —(CH$_2$ )p—X—B wherein p is zero and X is a bond. Preferably $R_1$, $R_2$ and $R_3$ in formula I are selected from H, OH, —NO$_2$, lower alkoxy, alkoxyalkoxy, lower alkyl lower alkandioyl, m-halogeno, N$R_{10}R_{11}$(lower alkoxy)-, allyloxy, phenoxy, alkoxycarbonylalkoxy and —C(O)$R_{12}$. Compounds of formula I wherein $R_1$ and $R_3$ are each H, and $R_2$ is in the para-position are more preferred.

$R_7$ in formula I is preferably selected from lower alkyl, lower alkoxy, halogeno, —OCF$_3$, lower alkylthio, —N$R_{10}R_{11}$, —CN, OH, and —COR$_{12}$. More preferred are compounds of formula I are those wherein n is 1 and $R_7$ is in the para-position.

A preferred β-lactam cholesterol absorption inhibitor is (3R-4S)-1,4-bis-(4-methoxyphenyl)-3-(3-phenylpropyl)-2-azetidinone.

The effectiveness of the combinations of this invention for the reduction of plasma cholesterol levels is demonstrated by the following test procedures. In the procedures, the β-lactam cholesterol absorption inhibitor is (3R-4S)-1,4-bis-(4-methoxyphenyl)-3-(3-phenylpropyl)-2-azetidinone (hereinafter Compound A) and the HMG CoA reductase inhibitor is lovastatin.

Experiment 1

Hypocholesterolemic effect of the combination of Compound A and lovastatin in the cholesterol-fed hamster Method:

Male Golden Syrian hamsters (Charles River Labs, Wilmington, Mass.) weighing between 100 and 125 g were fed Wayne rodent chow until study onset. At study onset (Day 1), animals were separated into groups (n=4–6/group) and fed Purina Chow #5001 supplemented with 0.5% by weight of cholesterol (Research Diets Inc., New Brunswick, N.J.). Compound A at 3 mg/kg and lovastatin at 10 mg/kg were administered once daily for 7 days, starting on Day 1 via oral gavage in 0.2 ml corn oil. On Day 7, animals were sacrificed by decapitation, blood was collected into tubes containing ethylenediaminetetraacetic acid (EDTA), and plasma was prepared by low speed centrifugation at 4° C.

Nonfasted plasma cholesterol levels were determined by a modification of the cholesterol oxidase method of Aliain et al. (Clin. Chem., 20 (1974) p. 470–475), in which the reagents were available in a kit form from Wako Pure Chemicals Industries, Ltd. (Osaka, Japan). Ten μl of serum was assayed for total cholesterol in 1 ml of 0.15M tris buffer, pH 7.0, containing p-chlorophenol (0.1%), cholesterol oxidase (0.13 U/ml), cholesterol ester hydrolase (0.13 U/ml), peroxidase (2.4 U/m l) and 4-aminoantipyrine (0.015%). Assays were carried out at 37° C. for 10 min, along with cholesterol standards, and the absorbance of the resultant red quinone pigment was determined spectrophotometrically at 505 nm.

Results:

Hamsters fed a 0.5% cholesterol-containing diet for 7 days showed a 2-fold increase in plasma cholesterol. The increase in plasma cholesterol is primarily in VLDL and LDL (Schnitzer-Polokoff et al, *Comp. Biochem. Physiol.,* 99A (1991) p. 665–670). Compound A at 3 mg/kg/day resulted in a 15% reduction in plasma cholesterol levels, while lovastatin had no effect at 10 mg/kg/day (Table 1). When Compound A and lovastatin were given in combination, a reduction in plasma cholesterol levels of 31% was found, which was significantly greater than either treatment alone (Table 1).

TABLE 1

| Group | Dose (mg/kg/day) | N | Hamster Plasma cholesterol (mg/dl) |
|---|---|---|---|
| Control | — | 6 | 227 ± 6 |
| Compound A | 3 | 4 | 192 ± 6[a] |
| Lovastatin | 10 | 4 | 223 ± 14 |
| Compound A + Lovastatin | 3<br>10 | 4 | 156 ± 11[a,b] |

Values are Means ± SEM.
[a] $p < 0.05$ compared to control group.
[b] $p < 0.05$ compared to either Compound A alone or lovastatin alone.

Experiment 2

Hypocholesterolemic effect of Compound A in combination with lovastatin in cholesterol-fed rabbits Methods:

Male New Zealand White rabbits weighing 2.4–2.6 kg were challenged for one week with a diet containing 1% cholesterol and 6% peanut oil. Hyper- and hypo-responding rabbits with serum cholesterol levels more than one standard deviation from the mean were excluded and four groups of rabbits with equivalent serum cholesterol levels were formed (n=8/group). The rabbits were then fed a diet containing 0.5% cholesterol and 6% peanut oil, alone or with 0.03% Compound A; 0.015% lovastatin; or 0.03% Compound A and 0.015% lovastatin. Non-fasting serum samples were obtained weekly for 4 weeks and serum cholesterol levels were determined as described in Experiment 1.

Results:

The one week challenge with the 1% cholesterol/6% peanut oil diet resulted in average serum cholesterol levels of approximately 1000 mg/dl (Table 2). Similar food consumption and weight gains were found among the four groups of rabbits over the 4 week study period. The dose of Compound A at 0.03% of the diet was calculated to be 14 mg/kg/day and the dose of lovastatin at 0.015% was 7 mg/kg/day. Serum cholesterol levels continued to rise in the control group from 1015 to 1358 mg/dl at the 4 week time point (Table 2). Compound A alone caused a 29% reduction in serum cholesterol at week 4 compared to week 0, while lovastatin alone caused a 33% reduction over the 4 week period, but these reductions over time were not statistically significant by ANOVA. The combination of Compound A with lovastatin caused statistically significant reductions in plasma cholesterol levels at all timepoints, with a 61% decrease at week 4 compared to week 0 (Table 2). The relative reductions in serum cholesterol levels were even greater when the 4 week values were compared to the control group, with a 47% decrease with Compound A alone, a 51% decrease with lovastatin alone, and a 72% reduction with the combined Compound A and lovastatin therapy.

TABLE 2

| | Rabbit Serum Cholesterol Levels (mg/dl) | | | | |
|---|---|---|---|---|---|
| Group | Week 0 | Week 1 | Week 2 | Week 3 | Week 4 |
| Control | 1015 ± 90 | 1138 ± 170 | 1316 ± 164 | 1437 ± 211 | 1358 ± 193 |
| Compound A (0.03% in diet) | 1005 ± 89 | 781 ± 122 | 879[a] ± 109 | 808[a] ± 121 | 713[a] ± 112 |
| Lovastatin (0.015% in diet) | 993 ± 95 | 895 ± 150 | 839[a] ± 80 | 767[a] ± 87 | 667[a] ± 81 |
| Compound A + Lovastatin (0.03% + 0.015% in diet) | 986 ± 93 | 552[a,b] ± 76 | 506[a,b] ± 58 | 427[a,b] ± 62 | 382[a,b] ± 66 |

Values represent means ± SEM with 8 rabbits/group.
[a] $p < 0.05$ compared to control group;
[b] $p < 0.05$ compared to Week 0 value by ANOVA over time for each treatment.

Experiment 3

Hypocholesterolemic effect of Compound A in combination with lovastatin in rhesus monkeys fed a cholesterol-free diet Methods:

Twenty rhesus monkeys (17 male, 3 female) weighing 4.4–8.5 kg were fed a fat-free monkey chow (Purina #5038-7) containing 5% corn oil for 2 weeks. Four groups of monkeys were formed with equivalent serum cholesterol levels and body weights (n=5/group). The monkeys were then continued on the fat-free chow containing 5% corn oil, alone or with 3 mg/kg/day Compound A; 20 mg/kg/day lovastatin; or Compound A (3 mg/kg/day) and lovastatin (20 mg/kg/day). Fasting serum samples were obtained weekly for 3 weeks and serum cholesterol levels were measured as described in Experiment 1. Statistical differences were determined by ANOVA and Dunnett t tests on the change in serum cholesterol levels. A probability level of $p<0.05$ was considered significant.

Results:

Control monkeys fed the fat-free chow containing 5% corn oil maintained a constant level of serum cholesterol over the three week study period (Table 3). Individually, Compound A at 3 mg/kg/day and lovastatin at 20 mg/kg/day caused slight reductions in serum cholesterol levels at 3 weeks, but these changes were not statistically significant compared to the 3-week control group. The combination of Compound A and lovastatin caused a significantly greater reduction of plasma cholesterol than either treatment alone at all timepoints and reached a 25% reduction at Week 3 (Table 3).

TABLE 3

| | Rhesus Monkey Serum Cholesterol Levels (mg/dl) | | | |
|---|---|---|---|---|
| Group | Week 0 | Week 1 | Week 2 | Week 3 |
| Control | 131 ± 1 | 129 ± 7 | 125 ± 8 | 132 ± 8 |
| Compound A (3 mg/kg/day) | 140 ± 10 | 122 ± 11 | 117 ± 7 | 125 ± 9 |
| Lovastatin (20 mg/kg/day) | 139 ± 7 | 127 ± 6 | 117 ± 5 | 120 ± 6 |

TABLE 3-continued

| Group | Rhesus Monkey Serum Cholesterol Levels (mg/dl) | | | |
|---|---|---|---|---|
| | Week 0 | Week 1 | Week 2 | Week 3 |
| Compound A + Lovastatin (3 + 20 mg/kg/day) | 136 ± 8 | 108* ± 7 | 101* ± 7 | 102* ± 8 |

Values represent means ± SEM with 5 monkeys/group.
*p < 0.05 compared to control group.

Experiment 4

Hypocholesterolemic effect of Compound A in combination with lovastatin in dogs fed a chow diet Methods:

Fifteen male beagles were divided into three groups with equivalent serum cholesterol levels and body weights (n=5/group). The dogs were fed Purina Dog Chow (#5006) containing maltodextrin and either 0.0234% Compound A; or 0.0234% lovastatin; or the combination of Compound A (0.0234%) and lovastatin (0.0234%) for seven days. Serum samples were obtained at Day 0, 3 and 7, and serum total cholesterol levels were measured as described in Experiment 1. Statistical differences were determined by ANOVA and a probability level of p<0.05 was considered significant.

Results:

Dogs fed the chow diet containing either Compound A at 0.0234% (5 mg/kg/day) or lovastatin at 0.0234% (5 mg/kg/day) resulted in serum cholesterol levels which were unchanged from baseline levels (Day 0) at Day 3 or Day 7 (Table 4). The combination of Compound A at 5 mg/kg/day and lovastatin at 5 mg/kg/day caused a 33% reduction in serum cholesterol levels at Day 7 compared to baseline at Day 0 (Table 4). The serum cholesterol levels in the combination group were also significantly lower than levels in either group administered Compound A or lovastatin alone at Day 7. (Table 4)

TABLE 4

| Group | Dog Serum Cholesterol Levels (mg/dl) | | |
|---|---|---|---|
| | Day 0 | Day 3 | Day 7 |
| Compound A (5 mg/kg/day) | 114 ± 5 | 106 ± 13 | 109 ± 10 |
| Lovastatin (5 mg/kg/day) | 107 ± 10 | 107 ± 8 | 114 ± 9 |
| Compound A + Lovastatin (5 mg/kg/day each) | 109 ± 8 | 89 ± 4 | 77$^{a,b}$ ± 3 |

Values represent means ± SEM with 5 dogs/group.
$^a$p < 0.05 compared to Day 0.
$^b$p < 0.05 compared to Day 7 values of either Compound A alone or lovastatin alone.

Since the present invention relates to a method of treatment comprising the administration of a combination of two components, the components can be co-administered simultaneously or sequentially, or a single pharmaceutical composition comprising a cholesterol biosynthesis inhibitor and a β-lactam cholesterol absorption inhibitor in a pharmaceutically acceptable carrier can be administered. The components of the combination can be administered individually or together in any conventional oral or parenteral dosage form such as a capsule, tablet, powder, cachet, suspension or solution. The formulations can be prepared using conventional pharmaceutical excipients and additives using conventional techniques. Such pharmaceutically acceptable excipients and additives include non-toxic compatible fillers, binders, disintegrants, buffers, preservatives, antioxidants, lubricants, flavorings, thickeners, coloring agents, emulsifiers and the like.

Representative formulations comprising a β-lactam cholesterol absorption inhibitor are disclosed in PCT/US92/05972 cited above. Representative formulations comprising a cholesterol biosynthesis inhibitor are well known in the art. It is contemplated that where the two active ingredients are administered as a single composition, the dosage forms as disclosed in the aforementioned PCT application may readily be modified using the knowledge of one skilled in the art.

The daily doses of the compounds in the combination of this invention for reducing plasma cholesterol levels are as follows: for cholesterol biosynthesis inhibitors, the typical dosage is 0.1 to 80 mg/kg of mammalian weight per day administered in single or divided dosages, usually once or twice a day; for the β-lactam cholesterol absorption inhibitor, the typical dosage is 0.1 to 10 mg/kg mammalian weight per day in single or divided dosages. The exact dose of any component of the combination to be administered is determined by the attending clinician and is dependent on the potency of the compound administered, the age, weight, condition and response of the patient.

Generally, to reduce the plasma cholesterol levels in mammals needing such treatment, the compounds in the combination of this invention may be administered to patients in dosage ranges as follows: for HMG CoA reductase inhibitors, about 10 to about 40 mg per dose is given 1 to 2 times a day, giving a total daily dose of about 10 to 80 mg per day, and for the other cholesterol biosynthesis inhibitors, about 1 to 1000 mg per dose is given 1 to 2 times a day, giving a total daily dose of about 1 mg to about 2 g per day. About 1 to about 1000 mg per dose of the β-lactam cholesterol absorption inhibitor is given 1 to 4 times a day. Where the components of a combination are administered separately, the number of doses of each component given per day may not necessarily be the same, e.g. where one component may have a greater duration of activity, and will therefore need to be administered less frequently.

Since the present invention relates to the reduction of plasma cholesterol levels by treatment with a combination of active ingredients wherein said active ingredients may be administered separately, the invention also relates to combining separate pharmaceutical compositions in kit form. That is, a kit is contemplated wherein two separate units are combined: a cholesterol biosynthesis inhibitor pharmaceutical composition and a β-lactam cholesterol absorption inhibitor pharmaceutical composition. The kit will preferably include directions for the administration of the separate components. The kit form is particularly advantageous when the separate components must be administered in different dosage forms (e.g. oral and parenteral) or are administered at different dosage intervals.

We claim:

1. A method of treating or preventing atherosclerosis or reducing plasma cholesterol levels comprising simultaneously or sequentially administering to a mammal in need of such treatment or prevention an effective amount of a cholesterol biosynthesis inhibitor selected from the group consisting of HMG CoA reductase inhibitors and a β-lactam cholesterol absorption inhibitor represented by the structural formula

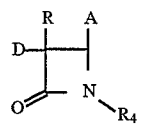

or a pharmaceutically acceptable salt thereof, wherein

D is B'—(CH$_2$)$_q$—, wherein B' is phenyl and q is 3 or 4;

B'—O—(CH$_2$)$_2$—, wherein B' is p-fluoro-phenyl or p-methoxyphenyl; 3-phenyl-1-propenyl or B'—(CH$_2$)—V—, wherein B' is phenyl and V is cyclopropylene;

A is —(CH$_2$)$_p$—X—B wherein p is zero, X is a bond and B is

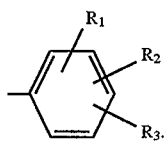

R$_1$, R$_2$ and R$_3$ are selected from the group consisting of H, lower alkoxy, alkoxyalkyl, alkoxyalkoxy, alkoxycarbonyl-alkoxy, lower alkyl lower alkanedioyl, allyloxy, phenoxy, OH, m-halogeno and —C(O)R$_{12}$;

R$_4$ is (R$_7$)$_n$-substituted phenyl, wherein n is 1 and R$_7$ is lower alkyl, lower alkoxy, halogeno, OH or —OCF$_3$; and R$_{12}$ is alkoxy.

2. The method as claimed in claim 1, wherein the β-lactam cholesterol absorption inhibitor is (3R-4S)-1,4-bis-(4-methoxy-phenyl)-3-(3-phenylpropyl)-2-azetidinone.

3. A method of claim 1 wherein the cholesterol biosynthesis inhibitor is selected from the group consisting of lovastatin, pravastatin, fluvastatin, simvastatin and atorvastatin.

4. A pharmaceutical composition for the treatment or prevention of athersclerosis, or for the reduction of plasma cholesterol levels, comprising a β-lactam cholesterol absorption inhibitor represented by the structural formula

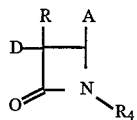

or a pharmaceutically acceptable salt thereof, wherein

D is B'—(CH$_2$)$_q$—, wherein B' is phenyl and q is 3 or 4;

B'—O—(CH$_2$)$_2$—, wherein B' is p-fluoro-phenyl or p-methoxyphenyl;

3-phenyl-1-propenyl; or

B'—(CH$_2$)—V—, wherein B' is phenyl and V is cyclopropylene;

A is —(CH$_2$)$_p$—X—B wherein p is zero, X is a bond and B is

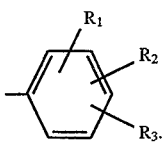

R$_1$, R$_2$ and R$_3$ are selected from the group consisting of H, lower alkoxy, alkoxyalkyl, alkoxyalkoxy, alkoxycarbonyl-alkoxy, lower alkyl lower alkanedioyl, allyloxy, phenoxy, OH, m-halogeno and —C(O)R$_{12}$;

R$_4$ is (R$_7$)$_n$-substituted phenyl, wherein n is 1 and R$_7$ is lower alkyl, lower alkoxy, halogeno, OH or —OCF$_3$; and R$_{12}$ is alkoxy, a cholesterol biosynthesis inhibitor selected from the group consisting of HMG CoA reductase inhibitors and a pharmaceutically acceptable carrier.

5. A pharmaceutical composition of claim 4 wherein the cholesterol biosynthesis inhibitor is selected from the group consisting of lovastatin, pravastatin, fluvastatin, simvastatin and atorvastatin.

6. A pharmaceutical composition of claim 4 wherein the β-lactam cholesterol absorption inhibitor is (3R-4S)-1,4-bis-(4-methoxy-phenyl)-3-(3-phenylpropyl)-2-azetidinone and the cholesterol biosynthesis inhibitor is selected from the group consisting of lovastatin, fluvastatin, atorvastatin, pravastatin and simvastatin.

7. A kit comprising in separate containers in a single package pharmaceutical compositions wherein said pharmaceutical compositions are combined to treat or prevent athersclerosis or to reduce plasma cholesterol levels which comprises in one container an effective amount of a cholesterol biosynthesis inhibitor selected from the group consisting of HMG CoA reductase inhibitors in a pharmaceutically acceptable carrier, and in a second container, an effective amount of a β-lactam cholesterol absorption inhibitor represented by the structural formula

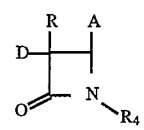

or a pharmaceutically acceptable salt thereof, wherein

D is B'—(CH$_2$)$_q$—, wherein B' is phenyl and q is 3 or 4;

B'—O—(CH$_2$)$_2$—, wherein B' is p-fluoro-phenyl or p-methoxyphenyl;

3-phenyl-1-propenyl; or

B'—(CH$_2$)—V—, wherein B' is phenyl and V is cyclopropylene:

A is —(CH$_2$)$_p$—X—B wherein p is zero, X is a bond and B is

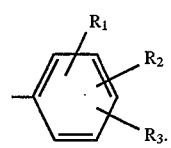

R$_1$, R$_2$ and R$_3$ are selected from the group consisting of H, lower alkoxy, alkoxyalkyl, alkoxyalkoxy, alkoxycarbonyl-alkoxy, lower alkyl lower alkanedioyl, aliyloxy, phenoxy, OH, m-halogeno and —C(O)R$_{12}$;

R$_4$ is (R$_7$)$_n$-substituted phenyl, wherein n is 1 and R$_7$ is lower alkyl, lower alkoxy, halogeno, OH or —OCF$_3$; and R$_{12}$ is alkoxy in a pharmaceutically acceptable carrier.

* * * * *